(12) United States Patent
Kang

(10) Patent No.: US 7,690,586 B2
(45) Date of Patent: Apr. 6, 2010

(54) DEODORIZER FOR REFRIGERATOR

(75) Inventor: Byeong-Gyu Kang, Gyeongsangnam-Do (KR)

(73) Assignee: LG Electronics Inc., Seoul (KR)

( * ) Notice: Subject to any disclaimer, the term of this patent is extended or adjusted under 35 U.S.C. 154(b) by 110 days.

(21) Appl. No.: 11/956,691

(22) Filed: Dec. 14, 2007

(65) Prior Publication Data

US 2008/0092563 A1    Apr. 24, 2008

Related U.S. Application Data

(62) Division of application No. 10/944,891, filed on Sep. 21, 2004, now abandoned.

(30) Foreign Application Priority Data

Sep. 30, 2003   (KR)   ................ 67803/2003

(51) Int. Cl.
*A24F 25/00*    (2006.01)
*A61L 9/04*    (2006.01)

(52) U.S. Cl. .................. 239/43; 239/51.5; 239/53; 239/57

(58) Field of Classification Search .......... 239/34, 239/41–43, 47, 51.5, 55, 57, 53; 62/199, 62/407, 408, 180

See application file for complete search history.

(56) References Cited

U.S. PATENT DOCUMENTS

| | | | | |
|---|---|---|---|---|
| 337,164 | A | 3/1886 | Kidney | 239/47 |
| 2,557,432 | A | 6/1951 | Holstedt | 96/148 |
| 4,161,284 | A | 7/1979 | Rattan | 239/43 |
| 4,416,119 | A * | 11/1983 | Wilson et al. | 62/149 |
| 4,535,935 | A | 8/1985 | Spector | 239/34 |
| 4,753,389 | A | 6/1988 | Davis | 239/6 |
| 4,815,659 | A | 3/1989 | Turko et al. | 239/6 |
| 4,869,734 | A | 9/1989 | Jacquish | 95/111 |
| 5,401,975 | A | 3/1995 | Ihara et al. | 250/492.3 |
| 5,478,505 | A | 12/1995 | McElfresh et al. | 26/130 |
| 5,549,247 | A | 8/1996 | Rossman et al. | 239/57 |
| 6,058,734 | A * | 5/2000 | Lee | 62/408 |
| 6,351,855 | B1 | 3/2002 | Allen | 42/213 |
| 6,767,521 | B1 | 7/2004 | Vogt et al. | 422/306 |

\* cited by examiner

*Primary Examiner*—Davis Hwu
(74) *Attorney, Agent, or Firm*—KED & Associates LLP

(57) ABSTRACT

A deodorizer for a refrigerator is formed of a mesh type material having fine multiple pores through which the air in the refrigerator passes and the material having multiple pleats so as to enlarge a surface area coming in contact with the air, thereby maximizing a surface area coming in contact with the cool air and accordingly, improving deodorizing performance.

6 Claims, 4 Drawing Sheets

DEODORIZER FOR REFRIGERATOR

CROSS-REFERENCE TO RELATED APPLICATIONS

This application is a Divisional Application of prior U.S. patent application Ser. No. 10/944,891 filed Sep. 21, 2004 now abandoned, which claims priority under 35 U.S.C. §119 to Korean Application No. 67803/2003 filed on Sep. 30, 2003, whose entire disclosures are hereby incorporated by reference.

BACKGROUND OF THE INVENTION

1. Field of the Invention

The present invention relates to a deodorizer for a refrigerator, and more particularly, to a deodorizer for a refrigerator capable of improving deodorizing performance by increasing a surface area coming in contact with the cool air.

2. Description of the Background Art

In general, a refrigerator maintains freshness of food items as cool air cooled by a freezing cycle is sent to a freezing compartment (chamber) and a refrigerating compartment (chamber) to freeze food items stored in the freezing compartment or to maintain food items stored in the refrigerating compartment at a low temperature.

In the refrigerating compartment, food items are stored at a temperature that is higher than a freezing point, unlike the freezing compartment in which the food items are stored in a frozen state. For this reason, the smell (odor) is generated from the food items stored in the refrigerating compartment. In order to remove such odor generated from various food items stored in the refrigerating compartment, a deodorizer is installed inside the refrigerating compartment.

FIG. 1 is a sectional view of a general refrigerator.

A general side by side type refrigerator includes a main body 10 having a receiving space therein; a freezing compartment 12 disposed at one of left and right sides of the main body 10, for keeping frozen items; and a refrigerating compartment 14 separated from the freezing compartment 12 by a mullion wall 16 and disposed at the other one of the left and right sides of the main body 10, for keeping cooled items.

A heat exchanger 18 by which air is cooled while passing therethrough, and a blowing fan 20 for forcedly sending the air cooled by the heat exchanger 18 into the refrigerating compartment 14 are installed at a rear upper wall of the freezing compartment 12.

A cool-air supply passage 22 through which the cool air is supplied from the blowing fan 20 into the refrigerating compartment 14 is formed at an upper side of the mullion wall 16, and a cool-air suction passage 24 through which the cool air, which has completed cooling operation while circulating inside the refrigerating compartment 14, is introduced to the heat exchanger 18 is formed at a lower side of the mullion wall 16.

The refrigerating compartment 14 is provided with a rear cool-air discharge duct 26 communicating with the cool-air supply passage 22 and installed at a rear wall of the refrigerating compartment, for discharging the cool air from the rear of the refrigerating compartment 14; a left cool-air discharge duct 28 installed at the left side of the refrigerating compartment 14, for discharging the cool air from the left side of the refrigerating compartment 14; and a right cool-air discharge duct 30 for discharging the cool air from the right side of the refrigerating compartment 14.

The cool-air suction passage 24 is installed with a deodorizer assembly 32 for removing the odor contained in the cool air which has completed cooling operation for food items stored in the refrigerating chamber while circulating inside the refrigerating chamber.

FIG. 2 is an exploded perspective view of a deodorizer assembly according to the conventional art.

The deodorizer assembly according to the conventional art includes a case 110 mounted at the cool-air suction passage 24 and having a receiving space 116 and a plurality of through holes 118 through which cool air passes; a deodorizer 114 mounted in the receiving space 116, for removing the odor when the cool air passes therethrough; and a cover 112 mounted at the case 110, protecting the deodorizer 114 and having a plurality of through holes 120 through which the cool air passes.

The deodorizer 114 has a rectangular parallelepiped shape with a certain thickness to be inserted in the receiving space 116 of the case 110, and a plurality of through holes 124 through which the cool air passes are formed at the deodorizer 114.

The operation of the deodorizer assembly according to the conventional art will now be described.

The cool air which has circulated inside the refrigerating chamber 14 is sucked through the through holes 120 of the cover 112 and passes through the through holes 124 formed at the deodorizer 114, whereby the odor contained in the cool air is removed. Then, the deodorized cool air by the deodorizer 114 is introduced to the cool-air suction passage 24 through the through holes 118 of the case 110.

However, the deodorizer assembly according to the conventional art has following problems.

Because the odor is removed while the cool air passes through the through holes 124 formed at the deodorizer 114, if an area of the through hole 124 is formed to be large, the odor of the cool air passing through the through hole 124 is partially removed, which results in deterioration of deodorizing performance. Also, if the area of the through hole 124 is formed to be small, flow resistance of the air is generated, and thus the air cannot be smoothly sucked therein.

SUMMARY OF THE INVENTION

Therefore, an object of the present invention is to provide a deodorizer for a refrigerator capable of improving deodorizing performance by forming a mesh type deodorizer and thus maximizing a surface area coming in contact with cool air.

To achieve these and other advantages and in accordance with the purpose of the present invention, as embodied and broadly described herein, there is provided a deodorizer for a refrigerator formed of a mesh type material having multiple pores through which the air in the refrigerator passes, and the material having multiple pleats so as to enlarge a surface area coming in contact with the air.

The material is formed by covering a surface of a support member, which has fine multiple pores and is repeatedly folded, with carbon nano balls performing deodorizing operation.

The support member is made of a fiber.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a unit of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

There may be a plurality of embodiments for a deodorizer for a refrigerator according to the present invention, and hereinafter, the most preferred embodiment will be explained.

Figure 3:
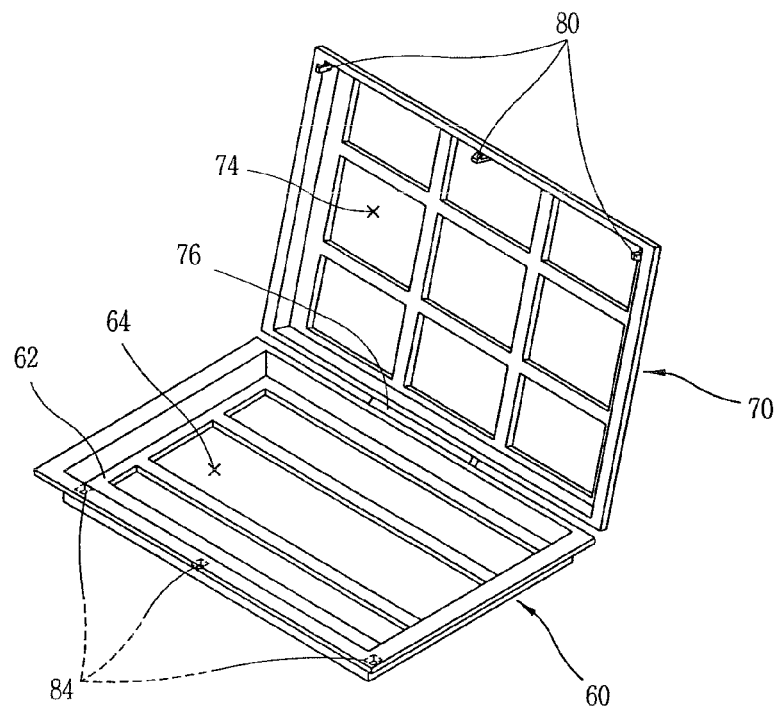
FIG. 3 is an exploded perspective view of a deodorizer for a refrigerator according to the present invention.
Figure 4:
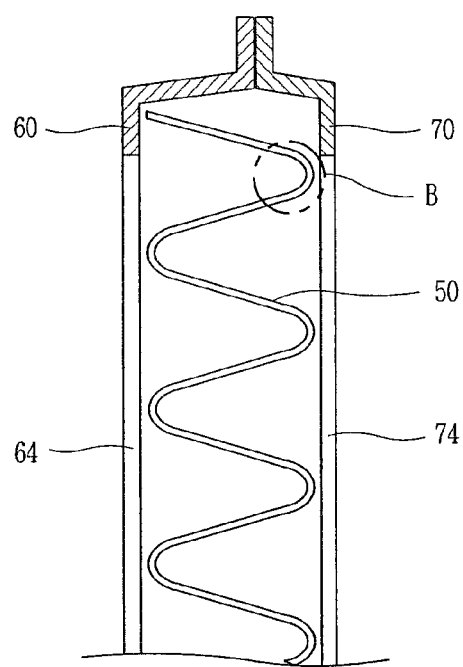
FIG. 4 is a sectional view of a deodorizer for a refrigerator according to the present invention.

FIG. 3 is an exploded perspective view of a deodorizer for a refrigerator according to the present invention, and FIG. 4 is a sectional view of a deodorizer for a refrigerator according to the present invention.

Figure 1:
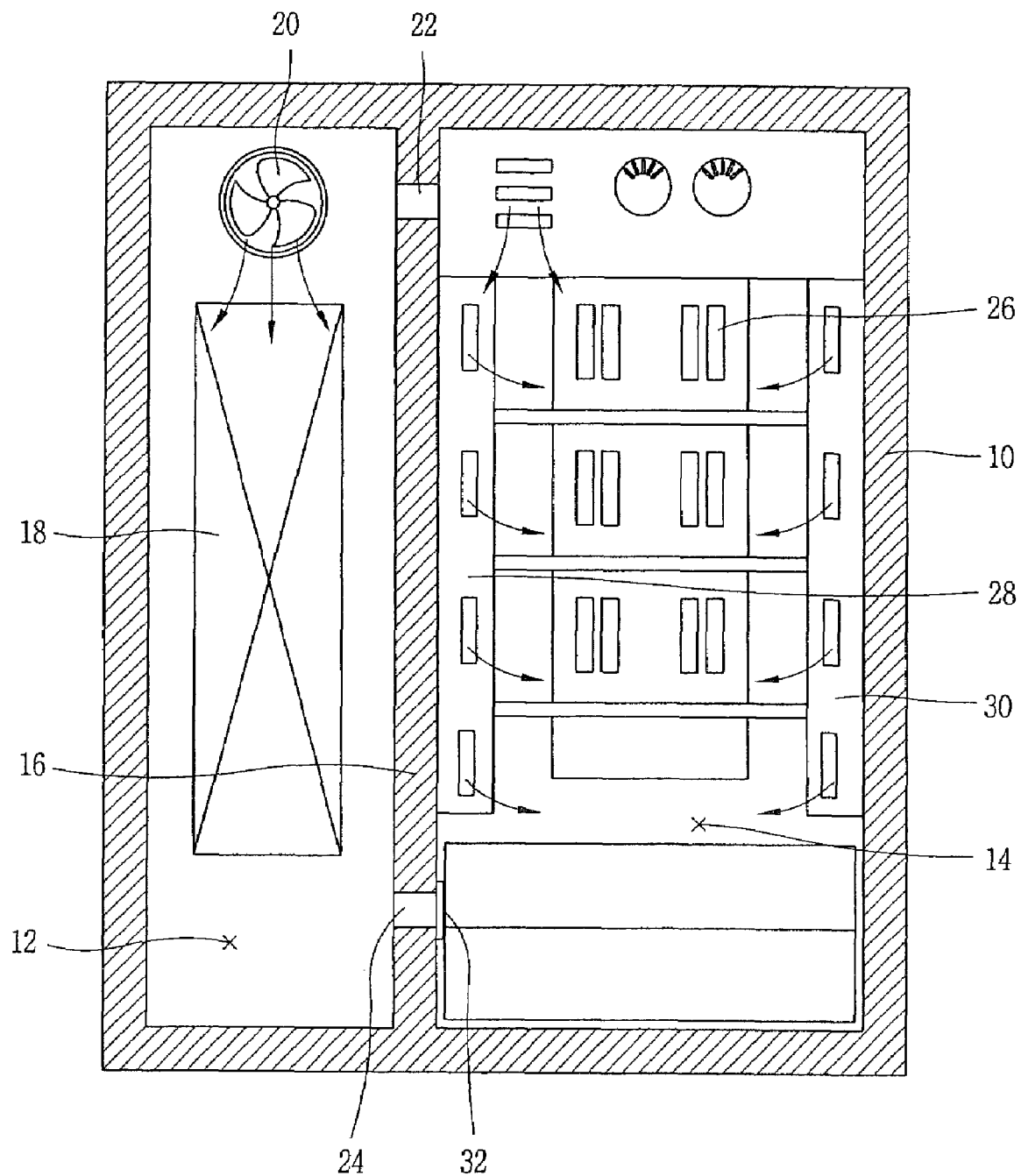
FIG. 1 is a sectional view of a general side by side type refrigerator.
Figure 2:
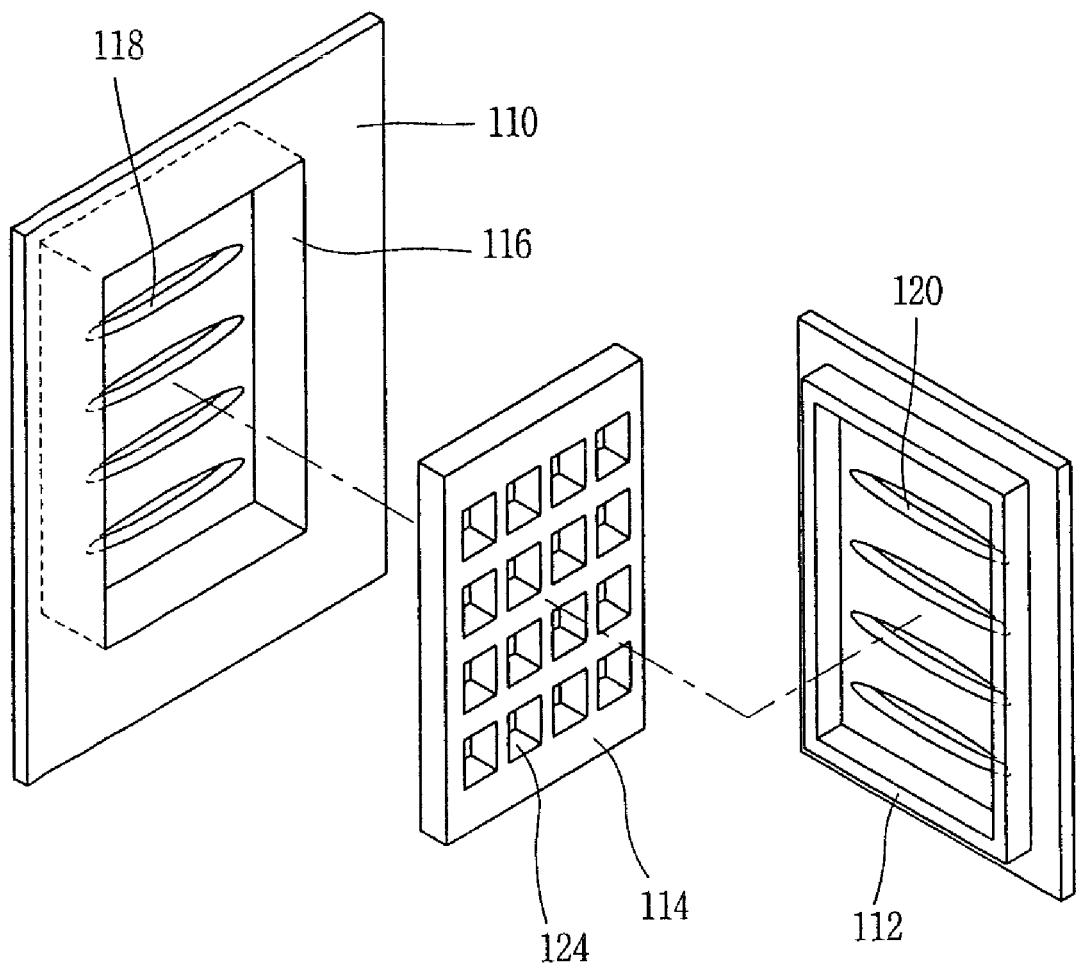
FIG. 2 is an exploded perspective view of a deodorizer for a refrigerator according to the conventional art.

Referring to FIG. 1, the refrigerator according to the present invention includes a main body 10 having a receiving space therein; a freezing compartment 12 disposed at one of left and right sides of the main body 10, for storing frozen food items; a refrigerating compartment 14 separated from the freezing compartment 12 by a mullion wall 16, disposed at the other one of the left and right sides of the main body 10, for storing cooled food items; and a deodorizer assembly 32 installed at one side of the refrigerating compartment 14, for removing the odor generated from the food items stored in the refrigerating compartment 14.

A heat exchanger 18 by which air is cooled while passing therethrough and a blowing fan 20 for forcedly sending the air cooled by the heat exchanger 18 are installed at a rear upper wall of the refrigerating compartment 12.

A cool-air supply passage 22 through which the cool air is supplied from the blowing fan 20 into the refrigerating compartment 14 is formed at an upper side of the mullion wall 16, and a cool-air suction passage 24 through which the cool air, which has completed its cooling operation while circulating inside the refrigerating compartment 14, is introduced to a heat exchanger 18 is formed at a lower side of the mullion wall 16.

The refrigerating compartment 14 is provided with a rear cool-air discharge duct 26 communicating with the cool-air supply passage 22 and installed at a rear wall of the refrigerating compartment 14, for discharging the cool air from the rear of the refrigerating compartment 14; a left cool-air discharge duct 28 installed at a left side of the refrigerating compartment 14, for discharging the cool air from the left side of the refrigerating compartment 14; and a right cool-air discharge duct 30 installed at the right side of the refrigerating compartment 14, for discharging the cool air from the right side of the refrigerating compartment 14.

Referring to FIGS. 3 and 4, the deodorizer assembly 32 is installed on the cool-air suction passage 24 and circulates inside the refrigerating compartment, removing the odor contained in the cool air which has completed cooling operation for food items stored in the refrigerating compartment. Such a deodorizer assembly may be installed at any position through which the cool air passes besides the cool-air suction passage 24.

Such a deodorizer assembly 32 includes a deodorizer 50 formed in a mesh type material having a plurality of fine pores 52; a case 60 having a receiving space having the deodorizer 50 therein, and mounted in the refrigerating compartment; and a cover 70 detachably mounted to the case 60, for preventing detachment of the deodorizer 50 from the case 60.

Here, the case 60 and the cover 70 are provided with cool-air passages 64 and 74. A hinge portion 76 for rotatably connecting the cover 70 to the case 60 is formed between the case 60 and the cover 70, a hook 80 is formed at the cover 70, and a hook hole 84 by which the hook 80 is hooked is formed at the case 60. In such a manner, the cover 70 is fixed to the case 60.

Figure 5:
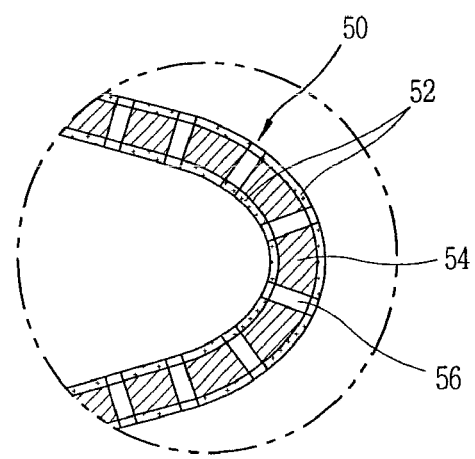
FIG. 5 is an enlarged view of part A of FIG. 4.
Figure 6:
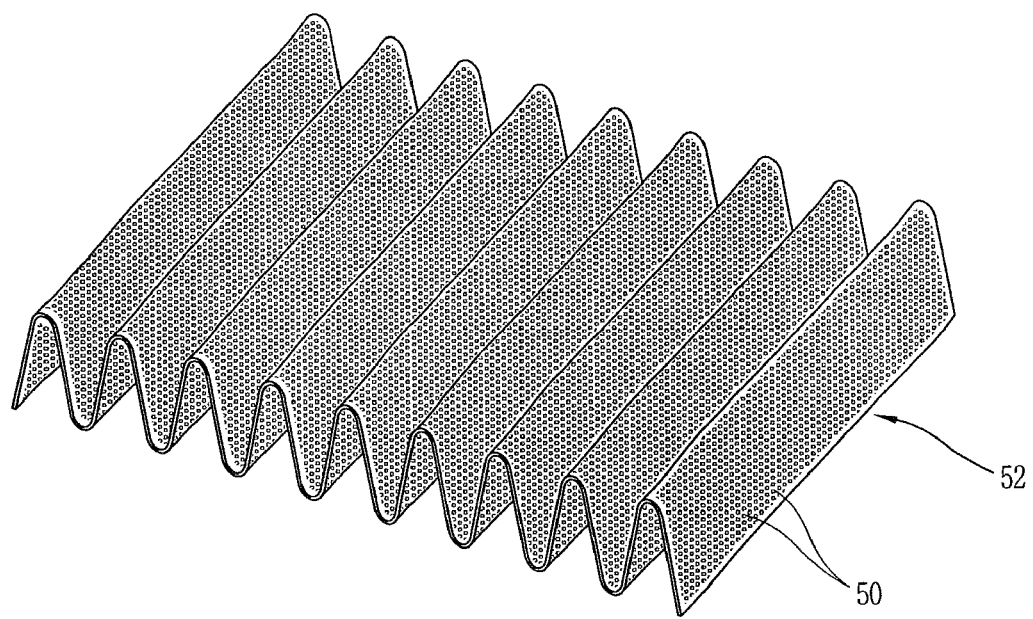
FIG. 6 is a perspective view of a deodorizer for a refrigerator according to the present invention.

As shown in FIGS. 5 and 6, the deodorizer 50 includes a support member 54 having fine multiple pores 52 and multiple pleats so as to maximize a surface area coming in contact with the cool air; and carbon nano balls 56 applied on a surface of the support member 54 by a spraying method, for removing the odor.

Here, preferably, the support member 54 is made of a fiber or a synthetic resin material.

The carbon nano ball 56 is a hollow carbon structure with a size of 200~500 nm and can effectively absorb bad smell components and an organic material in the air by having pores of a few nm and surface absorptive capacity. The carbon nano ball 56 has BET surface area (1450 $m^2/g$) which is about twice as much as activated carbon, a mesopore area (880 $m^2/g$) which is about six times as much as the activated carbon, and a pore volume (1.27 $cm^3/g$) which is about twice as much as the activated carbon. In comparison with the activated carbon, the carbon nano ball has a malodorous-gas removing force which is eight times as much as ammonia, ten times as much as methyl mercaptan and twelve times as much as timethylamine.

The operation of the deodorizer assembly according to the present invention will now be described.

A mesh type deodorizer 50 having fine multiple pores 52 is stored in the receiving space of the case 60, the case 60 is covered with a cover 70, and the hook 80 formed at the cover 70 is hooked by the hook hole 84 formed at the case 60, thereby completing assembly of the deodorizer assembly. Then, the assembled deodorizer assembly is mounted at the cool-air suction passage 14.

When the refrigerator is driven, the blowing fan 20 is rotated, supplying the cool air cooled by the heat exchanger 18 into the refrigerating compartment 14 through the cool-air supply passage 22. The supplied cool air performs cooling operation for various food items stored within the refrigerating compartment 14, and the cool air which has completed the cooling operation while circulating inside the refrigerating compartment 14 is re-circulated to the heat exchanger 18 through the cool-air suction passage 24. At this time, the cool air passes through the deodorizer assembly installed at the cool-air suction passage 24, thereby removing the odor contained in the cool air.

Here, because the deodorizer 50 is formed in a mesh type material having fine multiple pores 52, the cool air can pass therethrough with little flow resistance, making the smooth flow. Because the deodorizer 50 has a structure of being repetitively folded, a surface area coming in contact with the cool air can be maximized, thereby improving a deodorizing effect.

Effects of the deodorizer assembly for a refrigerator according to the present invention, constructed and operated as described above, will now be explained.

The deodorizer according to the present invention may maximize deodorizing capacity because carbon nano balls cover its surface to perform deodorization.

In addition, because the deodorizer is formed in a mesh type having fine multiple pores, flow resistance of the cool air is not generated, and thus the smooth flow of the cool air can be made.

Also, the deodorizer has a structure of being repetitively folded, so that a surface area coming in contact with the cool air can be maximized, improving deodorizing performance.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed:

1. A refrigerator, comprising:
    a main body having a refrigerating compartment and a freezer compartment, the refrigerating compartment having a plurality of cool-air discharge ducts and the freezer compartment having a heat exchanger and a blowing fan, and a cool air supply passage and a cool air suction passage providing communication between the refrigerating compartment and the freezer compartment; and
    a deodorizer assembly which is positioned adjacent the cool air suction passage, the deodorizer assembly comprising:
        a mesh type material, the mesh type material comprising:
            a support member having multiple pores, through which the air in the refrigerator passes, and having multiple pleats that enlarge a surface area in contact with the air; and
            a carbon nano ball coated on a surface of the support member to perform deodorization,
        a case having a plurality of cool air passages and a receiving space; and
        a cover having a plurality of cool air passages and configured to be attached to the case, wherein the mesh type material is positioned in the receiving space and retained therein by the cover, and wherein the carbon nano ball has a BET surface area of ~1450 $m^2/g$ which is about twice as much as activated carbon, a mesopore area of ~880 $m^2/g$ which is about six times as much as activated carbon, and a pore volume of ~1.27 $cm^3/g$ which is about twice as much as activated carbon.

2. The refrigerator of claim 1, wherein the cover is attached to the case by a hinge.

3. The refrigerator of claim 2, wherein the cover comprises at least one hook and the cover comprises at least one corresponding hole.

4. The refrigerator of claim 1, wherein the support member is made of fiber.

5. The refrigerator of claim 1, wherein the support member is made of a synthetic resin material.

6. The refrigerator of claim 1, wherein the carbon nano ball comprise a hollow carbon structure with a size of ~200~500 nm.

* * * * *